(12) United States Patent
Lever et al.

(10) Patent No.: US 8,298,826 B2
(45) Date of Patent: Oct. 30, 2012

(54) CHIMAERIC VECTOR SYSTEM

(75) Inventors: Andrew Michael Lindsay Lever, Cambridge (GB); Padraig Michael Strappe, Galway (IE)

(73) Assignee: Cambridge Enterprise Limited, Cambridge (GB)

( * ) Notice: Subject to any disclaimer, the term of this patent is extended or adjusted under 35 U.S.C. 154(b) by 1237 days.

(21) Appl. No.: 10/567,661

(22) PCT Filed: Aug. 9, 2004

(86) PCT No.: PCT/GB2004/003438
§ 371 (c)(1),
(2), (4) Date: Sep. 6, 2006

(87) PCT Pub. No.: WO2005/014836
PCT Pub. Date: Feb. 17, 2005

(65) Prior Publication Data
US 2007/0184025 A1 Aug. 9, 2007

(30) Foreign Application Priority Data
Aug. 8, 2003 (GB) .................................. 0318704.4

(51) Int. Cl.
*C12N 15/00* (2006.01)
*C12N 15/09* (2006.01)
*C12N 15/64* (2006.01)
*C12N 15/869* (2006.01)

(52) U.S. Cl. .................. 435/456; 424/93.6; 424/184.1; 435/455; 435/69.1; 514/44

(58) Field of Classification Search ........................ None
See application file for complete search history.

(56) References Cited

OTHER PUBLICATIONS

White et al, Lentivirus Vectors Using Human and Simian Immunodeficiency Virus Elements, JVi, 1999, pp. 2832-2840.*
White et al., "Lentivirus vectors using human and simian immunodeficiency virus elements," *J Virology*, vol. 73, No. 4, 2832-2840 (Apr. 1999).
Ranjbar et al., "Construction of infectious SIV/HIV-2 chimeras," *AIDS* (Hagerstown), vol. 14, No. 16, 2479-2484 (Nov. 10, 2000).
Kaye and Lever, "Nonreciprocal packaging of human immunodeficiency virus type 1 and type 2 RNA: A possible role for the p2 domain of Gag in RNA encapsidation," *J Virology*, vol. 72, No. 7, pp. 5877-5885 (Jul. 1998).
Rizvi and Panganiban, "Simian immunodeficiency virus RNA is efficiently encapsulated by human immunodeficiency virus type 1 particles," *J Virology*, vol. 67, No. 5, 2681-2688 (May 1993).
Browning et al., "Primate and feline lentivirus vector RNA packaging and propagation by heterologous lentivirus virions," *J Virology*, vol. 75, No. 11, 5129-5140 (Jun. 2001).

\* cited by examiner

*Primary Examiner* — Maria Marvich
(74) *Attorney, Agent, or Firm* — Klarquist Sparkman, LLP

(57) ABSTRACT

This invention relates to a process for producing a Simian Immunodeficiency Virus (SIV) encoding a heterologous gene, which process comprises infecting a host cell with a first vector which is capable of producing SIV capsid and a second vector comprising a Human Immunodeficiency Virus type 2 (HIV-2) packaging signal sufficient to package the second vector in the SIV capsid and a heterologous gene capable of being expressed by the vector; and culturing the host cell.

2 Claims, 5 Drawing Sheets

HIV-1 (HxB2)

HIV-2 (ROD)

SIV(mac)

CHIMAERIC VECTOR SYSTEM

CROSS REFERENCE TO RELATED APPLICATIONS

This is a §371 U.S. national stage of International Application No. PCT/GB2004/003438, filed Aug. 9, 2004, which claims the benefit of Great Britain Application No. 0318704.4, filed Aug. 8, 2003. Both applications are incorporated herein in their entirety.

FIELD OF THE INVENTION

This invention relates to vectors and their use in gene transfer. The vectors are based on retroviruses, adapted so that they cannot package their own RNA, and which can be used as infectious agents to transfer foreign genes, e.g. for somatic gene therapy.

BACKGROUND OF THE INVENTION

Modified viruses have been used to deliver genetic material to cells, both for research/development purposes and for clinical purposes. Some of the most successful gene transfer systems ('vectors') are based on retroviruses, and more recently, on lentiviruses, a subfamily of retrovirideae. Retroviral vectors have the advantages of being able to efficiently infect a broad range of cell types, and of being able to integrate the genetic material they carry (e.g. exogenous therapeutic genes) into the genome of the target cell (e.g. cells of the human patient). However, retroviral vectors can only infect dividing cells, and this limits their use.

Lentiviral vectors have a number of advantages over retroviral vectors including the ability to infect both dividing and non-dividing cells.

However, for both retroviral and lentiviral vectors there are concerns that the genetic homology between the packaging constructs and the constructs comprising the packageable vectors and/or other viral sequences, including sequences present in the cells in which the retroviral vectors are produced, could lead to recombination events that could generate a dangerous replicating virus.

These recombination events are particularly prone to occur in the cell line in which the vector is produced. This is because, in order for the cell line to produce the vector, it must contain certain viral sequences which express the proteins and other factors necessary to package the vector into a virus-like particle that then can infect cells, reverse transcribe RNA and integrate the proviral DNA into the host cell genome. Recombination between the vector and these 'helper' sequences may in theory produce a dangerous replicating virus.

Testing of lentiviral vector biosafety in appropriate animal models is a major concern associated with the use of lentiviral vectors in clinical trials. As HIV-1 only causes AIDS in humans, there is presently no animal model to test the safety of HIV-1 based vectors.

SUMMARY OF THE INVENTION

The present inventors have surprising found that a non-reciprocity exists between HIV-2 and SIV such that SIV Gag proteins can capture HIV-2 RNA vectors but that the reverse cannot occur. Using a packaging-defective SIV provirus vector, packaging-defective cell lines may be produced which generate chimaeric SIV/HIV-2 vectors for efficient introduction of a desired gene or genetic sequence into mammalian cells.

One aspect of the invention provides a process or method of producing a virus, in particular a chimaeric virus for use in gene therapy, comprising;

culturing a host cell which comprises one or more Simian Immunodeficiency Virus (SIV) nucleic acid sequences capable of producing an SIV capsid and which further comprises a vector comprising a Human Immunodeficiency Virus type 2 (HIV-2) packaging signal and a heterologous nucleic acid sequence;

said vector being packaged in the SIV capsid to produce a viral particle comprising the heterologous nucleic acid sequence.

In some embodiments, a method may comprise infecting the host cell which produces the SIV capsid with the vector.

In other embodiments, a host cell may be infected with a first vector which comprises the one or more Simian Immunodeficiency Virus (SIV) nucleic acid sequences capable of producing an SIV capsid and a second vector which comprises the human Immunodeficiency Virus type 2 (HIV-2) packaging signal and a heterologous nucleic acid sequence.

Accordingly, another aspect of the invention provides a process for producing a Simian Immunodeficiency Virus (SIV) encoding a heterologous gene, which process comprises infecting a host cell with a first vector which is capable of producing SIV capsid and a second vector comprising a Human Immunodeficiency Virus type 2 (HIV-2) packaging signal sufficient to package the vector in the SIV capsid and a heterologous gene capable of being expressed by the vector; and culturing the host cell.

Another aspect of the invention provides a process for making a producer cell for the generation of virus comprising:

infecting a host cell which comprises one or more Simian Immunodeficiency Virus (SIV) nucleic acid sequences capable of producing an SIV capsid with a vector comprising a Human Immunodeficiency Virus type 2 (HIV-2) packaging signal and a heterologous nucleic acid sequence.

The invention also extends to host cells and viruses produced by the processes of the invention and kits and vector systems for use in such methods. Pharmaceutical compositions may be formulated which comprise such host cells or viruses.

The viruses, nucleic acids and cells of the invention may be used in gene therapy. Thus, the invention provides a method of delivering a therapeutic or antigenic protein or peptide to an individual comprising administering to the individual an effective amount of a first and second vector as described above, a virus, nucleic acid or cell according to the invention, or a pharmaceutical composition according to the invention.

DESCRIPTION OF THE INVENTION

Figure 1:
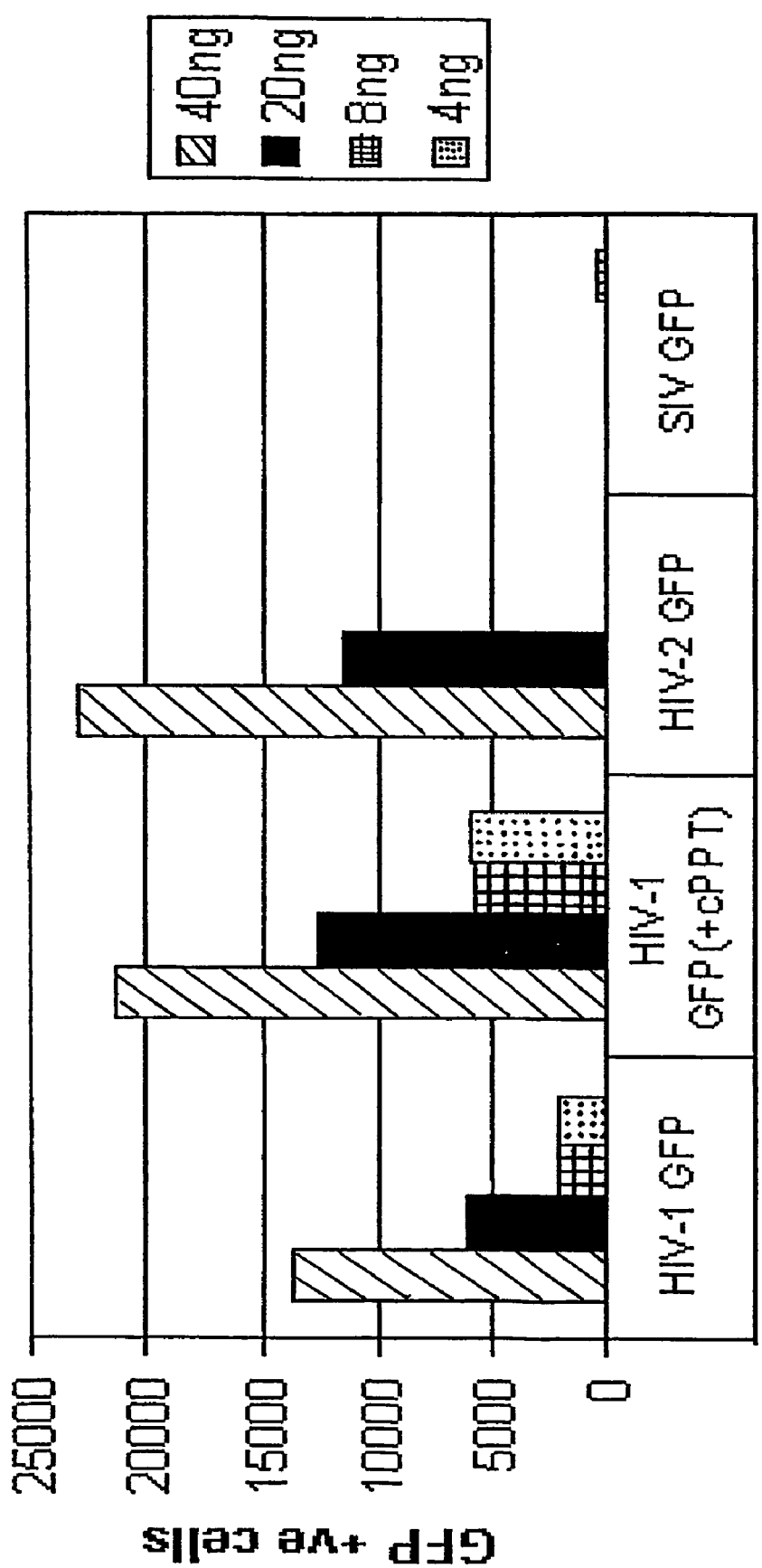
FIG. 1 shows the cross packaging efficiency of HIV-1 gag-pol (see table 2).

Packaging-defective proviral constructs are systems in which the provirus is capable of producing some viral proteins but is not replication-competent because the viral RNA cannot be packaged into virions. These constructs are commonly used to create packaging cell lines. The packaging defective proviral construct or constructs are known as the 'packaging constructs'. The RNA transcripts of the packaging constructs do not contain the sequences required for recognition and encapsidation into a viral particle. Introduction or expression of heterologous RNA transcripts containing the necessary packaging signal sequences into packaging cell lines results in the heterologous RNA being packaged into virions. A packaging cell line which produces virions comprising heterologous RNA is known as a producer line.

A producer line may, for example, contain the gag-pol sequences from SIV and a vector (i.e. a sequence of nucleic acid containing a packaging signal) derived from HIV-2. The producer line may also contain a sequence encoding an envelope protein from a non-SIV source. Suitable envelope proteins may be obtained from a variety of sources including, but not limited to, ecotropic retroviruses, amphotropic retroviruses, vesicular stomatitis virus (VSV) or any other kind of virus.

The env sequences may be part of the SIV proviral construct or, more preferably, may be located on a separate plasmid construct under control of a separate promoter and polyadenylation sequence in order to reduce homology and the possibility of recombination events.

The producer line may also contain one or more sequences encoding other proteins including but not limited to antibodies and antibody-like molecules, and any epitopes or subunits thereof, and any modified versions or fragments of any of the above. Modifications may include, but are not limited to, general post-translational protein modifications such as glycosylation (which might be dependent on the expression of native or exogenous glycosyltransferases or glycosylases or other enzymes in the producer line or in the supernatant).

The affinity of this gene transfer system for target cells may be provided by the envelope sequences, while the efficient reverse transcription and integration functions may be provided by the SIV gag-pol. Efficient packaging may be provided by a combination of the SIV gag-pol and the HIV-2 vector sequences. This combination would give rise to superior gene transfer efficiency as compared with many other systems.

The use of gag-pol and vector sequences from SIV and HIV-2 (and, optionally, an envelope gene from a third source) respectively may be useful in reducing the recombination probability, thereby increasing the safety of the system relative to other viral vector systems.

The superior safety and efficiency features derived from the combination of SIV and HIV-2 sequences, combined with the general advantages of lentiviral vectors (e.g. stable, long-term expression in dividing and non-dividing human cells and minimal disruption of the endogenous human genetic material) provide a gene transfer system with improved safety, efficiency and stability of expression in human cells.

Packaging Defective SIV Vectors

SIV packaging-defective vectors may be produced using standard techniques. The region between the primer-binding site and the 5' major splice donor in SIV contains sequences necessary for efficient packaging of SIV RNA into virions (Strappe, P. M. et al. *J. Gen Virol* (2003) 84:2423-2430). In addition, the region between the 5' major splice donor and the gag initiation codon contains a second and less important region, important but not essential for packaging of SIV RNA into virions. A vector comprising a packaging-defective SIV provirus may be prepared wherein the vector contains a nucleotide sequence which corresponds to a sufficient number of nucleotides from an SIV genome to express desired SIV products, but does not correspond to a sufficient number of nucleotides corresponding to the region between the primer-binding site and the 5' major splice donor or between the splice donor and the gag initiation codon to efficiently package SIV RNA (the packaging sequence). In other words, a vector may comprise SIV nucleic acid sequences which allow expression of desired SIV products, in particular SIV gag-pol, but may not comprise SIV nucleic acid sequences which allow efficient packaging of SIV RNA.

These sequences preferably correspond to the genome of SIV. The term 'corresponds' means that conservative additions, deletions and substitutions are permitted. The primer-binding site (23 bp) and the 5' major splice donor are respectively numbered 121-143 and 295-296 in the SIV genomic nucleotide sequence, where the transcript start site is defined as 1. In the SIVmac32H sequence (Acc No D01065) the primer-binding site and the 5' major splice donor are respectively numbered 822-849 and 985-986, where the first nucleotide of the 5'LTR is defined as 1. The genomic sequences of examples of other strains of SIV are set out in Table 5.

In particular, an SIV genome as used herein refers to the viral RNA derived from an SIV. The simian immunodeficiency viruses (SIV) of the invention may be derived from any SIV strain, for example a strain having a genomic sequence set in Table 5, or derivatives thereof. Derivatives preferably have at least 70% sequence homology to the SIV genome, more preferably at least 80%, even more preferably at least 90 or 95%.

Sequence homology may also be expressed in terms of sequence similarity or sequence identity. Sequence similarity and identity are commonly defined with reference to the algorithm GAP (Genetics Computer Group, Madison, Wis.). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) *J. Mol. Biol.* 215: 405-410), FASTA (which uses the method of Pearson and Lipman (1988) *PNAS USA* 85: 2444-2448), or the Smith-Waterman algorithm (Smith and Waterman (1981) *J. Mol Biol.* 147: 195-197), or the TBLASTN program, of Altschul et al. (1990) supra, generally employing default parameters. In particular, the psi-Blast algorithm (Nucl. Acids Res. (1997) 25 3389-3402) may be used. Sequence identity and similarity may also be determined using Genomequest™ software (Gene-IT, Worcester Mass. USA).

Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Particular amino acid sequence variants may differ from a known polypeptide sequence as described herein by insertion, addition, substitution or deletion of 1 amino acid, 2, 3, 4, 5-10, 10-20 20-30, 30-50, or more than 50 amino acids.

Sequence comparisons are preferably made over the full-length of the relevant sequence described herein.

Other derivatives which may be used to obtain the viruses of the present invention include strains that already have mutations in some SIV genes such as a mutation in the nef gene as described in Rud et al 1994 J. Gen Virol 75, 529-543. Other mutations may also be present as set out in more detail below. The position of the primer binding site and 5' major splice donor site can readily be established by one skilled in the art by reference to the published SIV sequences or for example by aligning a variant SIV to the sequences set out in Table 5.

In some preferred embodiments, a SIV genome has a mutation within the packaging signal such that the SIV RNA is not packaged within the SIV protein coating or capsid i.e. the mutation prevents packaging of the SIV genome). Preferably, such an SIV genome is capable of producing an SIV capsid.

The packaging regions of SIV are well known in the art and the skilled person is readily able to produce packaging deficient mutations using standard techniques. In some preferred embodiments, the packaging defective genome does not contain the SIV packaging sequences which correspond to the segments immediately downstream of the primer-binding site and just upstream of the 5' major splice donor of the SIV genome (residues 849-985 numbered from the 5'LTR) and/or those immediately downstream of splice donor and immediately upstream of the gag gene (residues 985-1054 numbered from the 5'LTR).

In some embodiments, the vector may contain nucleotides ranging from about 20 bases downstream of the primer-binding site to about 80 bases downstream of the primer-binding site and still be packaging-deficient (for example, nucleotides ranging from residue 869 to residue 929, numbered from the 5'LTR) and/or about 20 bases downstream of the major splice donor to 70 bases downstream (for example, nucleotides ranging from residues 1005 to 1054).

Preferably, the packaging sequence absent from the vector comprises all or part of the region between the primer binding site and the 5' major splice site (for example, residues 849-985 numbered from the 5'LTR).

In some embodiments, the packaging sequence absent from the vector in this region may contain or comprise the 85-base nucleotide sequence of SEQ ID No. 2 i.e. AGAACTCCTGAGTACGGCCTGAGTGAAG-GCAGTAAGGGCGGCAGGAACCAACCAC-GACGGAGTGCT CCTATAAAGGCGCAGGTCG.

The mutation of the SIV genome may comprise a deletion of:

(a) the sequence of SEQ ID NO: 2, or (b) a fragment thereof of 5 or more nucleotides in length, or (c) a variant of either (a) or (b).

A variant of the sequence of SEQ ID NO: 2 may include the corresponding sequence derived from a variant SIV genome, which may be identified for example by identifying the major 5' splice donor site, primer binding site or gag initiation codon and aligning the sequence of the variant to SEQ ID NO: 2 to identify the corresponding sequence of the variant SIV genome to SEQ ID No 2. Such a variant sequence may show at least 70% sequence homology to SEQ ID NO: 2, more preferably at least 80%, even more preferably at least 90 or 95%.

One preferred variant of SEQ ID NO: 2 may have the sequence of residues 854 to 937 of accession number D01065.1.

In preferred embodiments, the packaging signal comprises part or all of the region of the genome 5' to the major splice donor site, for example a region commencing 90, 80, 70, 60 or 50 nucleotides upstream of (5' to) the 5' major splice donor site (at position 985 numbered from the 5' LTR), extending to 40, 30, 20 or 10 nucleotides upstream of (5' to) the 5' major splice donor site. The mutation may comprise deletion or mutation within this region, for example to modify or delete 5, 10, 15, 20, 30, 40, 50 or 60 or more nucleotides from this region, preferably contiguous nucleotides. For example the packaging deletion may comprise nucleotides 53 to 85 of SEQ ID No 2.

This region of the SIV genome is the structural fold termed DIS and is associated with a palindromic terminus. In some preferred embodiments, the packaging sequences in this region are mutated to disrupt the formation of the palindromic terminus and thus remove the DIS structure.

In some embodiments, other SIV genomic sequences, such as those downstream of the 5' major splice donor site extending up to the gag initiation codon may be deleted. Preferably, such sequences are deleted in addition to the mutation of sequences upstream of the major splice donor. For example, the virus genome may have a deletion or mutation of all or part of the 50-base segment sequence shown as SEQ ID No. 3, i.e. GAAATAGCTGTCTTGTTACCAGGAAGG-GATAATAAGATAGATTGGGAGAT, or the corresponding sequence from a different SIV strain (e.g. nucleotides 1006-1054 of Acc No: D01065.1).

The number of bases that need to be deleted or mutated can vary greatly. For example, the given 50 or 85-base pair deletions in SIV are sufficient to result in loss of packaging ability. However, even smaller deletions in this region may result in loss of packaging efficiency. A deletion as small as about 5, 10, 15, 20 or 30 or more bases in this region and in particular a deletion in the region of nucleotides 53 to 85 of SEQ ID No 2, or a corresponding sequence, can remove efficient packaging ability. The size of a particular deletion to reduce or abrogate packaging ability can readily be determined based on the present disclosure by the person of ordinary skill in the art.

A mutation may comprise a deletion or modification of the sequence of SEQ ID NO: 2. An appropriate modification may comprise a substitution, addition and/or deletion. An appropriate mutation will be one which leads to a reduction in the ability of viral RNA to be packaged within an SIV capsid. Preferably, such a mutation will lead to viral RNA not being packaged within an SIV capsid.

The mutation may alternatively comprise deletion or modification of a fragment of SEQ ID NO: 2 or a variant thereof of 5 or more nucleotides in length. Such a fragment may be an internal fragment, that is to say, a deletion of 5 or more nucleotides within SEQ ID NO: 2, not including the end nucleotides of SEQ ID NO: 2. Such a fragment may be, for example, 5, 10, 15, 20 or 25 nucleotides in length. In the alternative, the fragment may comprise a fragment of 17 or more nucleotides in length, selected from any portion of SEQ ID NO: 2 or a variant thereof including a terminal fragment thereof. Such a fragment may be, for example, 15, 25, 35, 45, 55, 65 or 75 nucleotides in length.

Alternatively, larger deletions may be incorporated. Preferably, a larger deletion will comprise the 85 base nucleotide region shown in SEQ ID NO 2 or a variant thereof and will extend from this location in the SIV genome in one or both directions. Such a deletion may comprise a deletion of, for example, 1, 2, 5, 10, 20, 30, 50 or more bases at one or both ends of this sequence.

As described above, the vector preferably contains an SIV nucleotide segment containing a sufficient number of nucleotides corresponding to nucleotides of the SIV genome to express functional SIV gene products, but as described above, should not contain a sufficient number of nucleotides corresponding to the region between the primer-binding site and the 5' major splice donor or between 5' major splice donor and gag gene to permit efficient packaging of the viral RNA into virions. In other words, the vector preferably comprises an SIV nucleic acid sequence encoding functional SIV gene products, such as gag and pol, to produce an SIV capsid as described above, but does not contain an SIV packaging region which allows efficient packaging of the viral RNA into virions.

In establishing SIV packaging-defective cell lines, it is preferred that such cell lines do not produce any infectious SIV. Although a cell line transformed by these packaging-defective deficient vectors would have low infectivity because the cells are packaging-defective, some RNA can still be packaged into the virion. Accordingly, it is preferable that the SIV nucleotide segment or nucleic acid sequence in the vector does not correspond to the entire SIV genome so that, if some of the viral RNA is packaged into the virion, what is packaged will not be replication-competent virus.

The SIV genome as used herein refers to the viral RNA derived from an SIV. The SIV be derived from any SIV strain, or derivatives thereof. Examples of genomic sequences of different strains of SIV are shown in Table 5. Derivatives preferably have at least 70% sequence homology to the SIV genome, more preferably at least 80%, even more preferably at least 90 or 95%. Other derivatives which may be used to obtain the viruses of the present invention include strains that already have mutations in some SIV genes. Other mutations may also be present as set out in more detail below. The position of locations such as the primer binding site and 5' major splice donor site can readily be established by one skilled in the art by reference to the published SIV sequences or for example by aligning a variant SIV to the sequences set out and described herein.

Vectors Comprising HIV-2 Packaging Sequences

The vectors comprising HIV-2 packaging sequences may be packaged, as described herein, by the SIV envelope or heterologous viral envelopes such as the Amphotrophic Murine Leukaemia Virus envelope, Vesicular Stomatitis Virus G protein (VSV-G) or other Rhabdovirus envelopes. These vectors may be capable of being packaged by HIV-1 and/or HIV-2.

The invention encompasses a vector for expression of a heterologous gene which may be packaged into the SIV genome through the use of HIV-2 packaging sequences. Such a vector may comprise any suitable vector compatible with the proposed administration or use of the virus, which has an HIV-2 packaging sequence incorporated therein. Preferably, the vector is derived from the HIV-2 genome but includes mutation in one or more HIV-2 genes, for example, to render the HIV-2 genome replication deficient.

A suitable HIV-2 vector should contain a sufficient number of HIV-2 nucleotides (i.e. contiguous nucleotides from the HIV-2 genome) to permit efficient packaging of the viral RNA into virions.

HIV-2 has been described in a number of references. For example, McCann and Lever (1997) disclose pSVR which is in an infectious proviral clone of the ROD strain of HIV-2 containing the replication origin of simian virus 40. HIV-2 nucleotide positions herein are numbered relative to the first nucleotide of the viral RNA, that is, the transcript start site is defined as 1. Other examples of strains of HIV-2 are shown in Table 6.

HIV-2 packaging sequences have also been described in the art (Griffin, S. D. C et al, J. Virol. 2001).

SEQ ID NO: 1 comprises positions 380-408 of the HIV-2 RNA and has been demonstrated as being important for packaging of HIV-2. The 28 based nucleotide sequence of SEQ ID NO: 1 is: AACAAACCACGACGGAGTGCTCCTAGAA.

Preferably, a HIV-2 vector of the invention comprises an HIV-2 genome which comprises at least (a) SEQ ID NO: 1 or a fragment thereof, (b) an internal fragment thereof of 5 or more contiguous nucleotides in length, or (c) a fragment thereof of 17 or more contiguous nucleotides in length. SEQ ID NO: 1 also corresponds to residues 378-406 of HIV2 strain ROD (M15390.1).

A suitable vector may comprise a complete HIV-2 packaging signal or a sequence of SEQ ID NO: 1 comprising one or more modifications. An appropriate modification may comprise a substitution, addition and/or deletion. An appropriate modification will be one which retains the ability of viral RNA to be packaged within an HIV-2 capsid. The skilled person can easily determine whether or not this packaging occurs for any given sequence.

In some embodiments, the vector may comprise a partially deleted or modified fragment of SEQ ID NO: 1, or a variant thereof, of 5 or more nucleotides in length. Such a fragment is preferably an internal fragment, that is to say, a fragment of 5 or more contiguous nucleotides within SEQ ID NO: 1, not including the end nucleotides of SEQ ID NO: 1. Such a fragment may be, for example, 5, 10, 15, 20 or 25 nucleotides in length. In the alternative, the fragment may comprise a fragment of 17 or more nucleotides in length, selected from any portion of SEQ ID NO: 1 or a variant thereof including a terminal fragment thereof. Such a fragment may be, for example, 17, 19, 21, 23, 25, or 27 nucleotides in length.

Alternatively, larger portions of the HIV-2 genome may be incorporated. Preferably, such a larger portion will comprise positions 380-408 of the HIV-2 RNA and will extend from this location in one or both directions. Such a portion may comprise, for example, 1, 2, 5, 10, 20, 30, 50 or more bases at one or both ends of this sequence. This region of the HIV-2 genome includes a proposed structural fold, and is associated with a palindromic terminus. Preferably the deletion will allow the formation of the palindromic terminus. Preferably the vector will comprise a sequence lying between the primer binding site and this proposed structural fold.

A variant of the sequence identified in SEQ ID NO; 1 is a corresponding sequence derived from a variant HIV-2 genome which may be identified, for example, by identifying the major 5' splice donor site, primer binding site or gag initiation codon of a variant HIV-2 genome and aligning the sequence of the variant to SEQ ID NO: 1 or to the sequence of the HIV-2 genome described in McCann and Lever (supra) to identify the corresponding sequence of the variant HIV-2 genome to SEQ ID NO: 1. A variant preferably have at least 70% sequence homology to the SEQ ID NO: 1, more preferably at least 80%, even more preferably at least 90 or 95%. Sequence homology is discussed elsewhere herein.

The HIV-2 genome as used herein refers to the viral RNA derived from human immunodeficiency virus type 2 (HIV-2). HIV-2 may be derived from any HIV-2 strain, for example an HIV-2 genome set out in Table 6, or derivatives thereof. Derivatives preferably have at least 70% sequence homology to the HIV-2 genome, more preferably at least 80%, even more preferably at least 90 or 95%. Other derivatives which may be used to obtain the viruses of the present invention include strains that already have mutations in some HIV-2 genes. Other mutations may also be present as set out in more detail below. The position of locations such as the primer binding site and 5' major splice donor site can readily be established by one skilled in the art by reference to the published HIV-2 sequences or for example by aligning a variant HIV-2 to the sequences set out and described herein.

The packaging sequences which are present in such a vector may correspond to those sequences which are mutated to produce a packaging defective HIV-2 vector. Preferably, a substantial portion of the packaging signal is included. In a preferred aspect, the packaging sequence comprises the sequence of SEQ ID NO: 1, or a fragment thereof or a variant thereof. All of the HIV-2 sequences described above are preferred sequences for incorporation into a vector such that the vector can be packaged by an SIV capsid or protein envelope.

Alternatively and/or additionally to the packaging sequences described above, further HIV-2 packaging sequences may be present in a vector. These sequences may comprise 10, 20, 50, 100, 200, 300 or 400 or more polynucleotides from a region downstream of the 5' splice donor site. In a preferred aspect, these packaging sequences comprise the 5' part of gag, preferably comprising the matrix (MA) region of the gag ORF. In a preferred aspect, the packaging sequence comprises the sequence that lies between positions 553 and 912 of the HIV-2 RNA, or a variant thereof. A variant of such a packaging sequence is a corresponding sequence derived from a variant HIV-2 genome which may be identified, for example, by identifying the major 5' splice donor site, primer binding site or gag initiation codon of a variant HIV-2 genome and aligning the sequence of the variant to the sequence of the HIV-2 genome described in McCann and Lever (supra) to identify the corresponding sequence of the variant HIV-2 genome to SEQ ID NO: 1.

These vectors may be useful in efficiently packaging desired genetic sequences and delivering them to target cells. This may be done by preparing a vector containing a nucleotide segment containing a sufficient number of nucleotides corresponding to the packaging nucleotides of HIV-2 (HIV-2 packaging region), a predetermined gene and, flanking the packaging sequence and predetermined gene, sequences corresponding to a sufficient number of sequences from within and near the LTR for packaging, reverse transcription, integration of the vector into target cells and gene expression from the vector.

The packaging region preferably corresponds to at least the sequence of SEQ ID NO: 1. The vector might also comprise the 5' part of gag, preferably including the matrix (MA) sequence of HIV-2 in order to enhance packaging efficiency. For example, a sufficient number of HIV-2 sequences to be packaged, reverse-transcribed, integrated into and expressed in the target cells would include the U3, R and U5 sequences of the LTRs, the packaging sequences, the polypurine tract, the primer binding site and, optionally, the DNA 'flap sequence. Mutation of the gag initiation codon might be acceptable to avoid translation starting from this point whilst still retaining the cis acting gag nucleotide sequence required for packaging. For example, the gag ATG may be changed to ATC by site-directed mutagenesis.

When this vector is used to transfect an SIV packaging-deficient cell, it is the nucleotide sequence from this vector that will be packaged in the virions produced. These packaged genes may then be targeted to cells.

For example, the vector could contain a sufficient number of nucleotides corresponding to both 5' and 3' LTRs of HIV-2 to be expressed, reverse-transcribed and integrated and a sufficient number of nucleotides corresponding to the HIV-2 packaging sequences to be packaged. The vector would also contain a sufficient number of nucleotides of the gene which is desired to be transferred to produce a functional gene (e.g. gene segment). This gene can be any gene desired, as described below. The vector may also contain sequences corresponding to a promoter region which regulates the expression of the gene. The vector may be a self-inactivating vector, for example a self-inactivating retroviral vector. This may comprise a mutation in the U3 region of the 3'LTR of the vector which, after infection of the target cell during reverse transcription, is copied so that the 5' LTR contains this inactivating mutation, and the long terminal repeat promoter is inactivated. This leaves any internal promoter to function independently of any competition.

Host Cells

In the methods described herein, host cells are generated which produce SIV virus containing a vector for expression of a heterologous gene. The viruses are produced by co-transfecting a cell, such as a mammalian cell, with a vector which is capable of producing an SIV capsid, for example a packaging defective SIV vector, and a vector having an HIV-2 packaging signal and a heterologous gene.

Preferably, a selected cell line is transformed using at least two different vectors. By co-transfecting a cell with each vector, the cell is able to express all the viral structural and enzymatic proteins and produce virions.

The, or each, vector may be a self-inactivating vector. As described above, this may, for example, comprise a mutation in the U3 region of the 3'LTR of the vector which, after infection of the target cell during reverse transcription, is copied so that the 5' LTR contains this inactivating mutation and the long terminal repeat promoter is inactivated. This leaves any internal promoter to function independently of any competition.

Selection of particular promoters and polyadenylation sequences can readily be determined based upon the particular host cell. Preferably the polyadenylation sequences do not correspond to the 3'LTR.

In some embodiments, one vector may include sequences permitting expression of proteins upstream of env and the other vector may permit expression of the remaining proteins. For example, one vector may contain a nucleotide segment corresponding to a sufficient number of nucleotides upstream of the gag initiation codon to the env gene sequence to express the 5'-most gene products. In other words, the vector may comprise a nucleic acid sequence from the region upstream of the gag initiation codon to the env gene sequence which allows expression of the 5'-most gene products. The other vector may contain a nucleotide segment corresponding to a sufficient number of nucleotides downstream of the gag gene sequence and including a functional env gene sequence. In other words, the other vector may comprise a nucleic acid sequence from the region downstream of the gag gene sequence which includes a functional env gene sequence. Such vectors may be chemically synthesised using standard techniques from the reported gene sequence of the HIV-2/SIV genome or derived from the many available HIV-2/SIV proviruses using standard recombinant techniques, for example by taking advantage of the known restriction endonuclease sites in these viruses.

Preferably, each vector comprises a different marker gene. Then, using a pre-selected cell line co-transfected with these different vectors, and by looking for a cell containing both markers, a cell that has been co-transfected with both vectors may be found. Such a cell is able to produce all of the retroviral proteins. Although virions are produced, the RNA corresponding to the entire viral sequences are not packaged in these virions.

In some embodiments, more than two vectors may be employed. For example, a gag/pol vector, a protease vector and an env vector may be used.

Retroviruses may be pseudotyped with the envelope glycoproteins of other viruses. In some embodiments, a vector may contain a sufficient number of nucleotides to correspond to an env gene from a different retrovirus i.e. the vector may comprise an env gene from a different (non-SIV) retrovirus.

Preferably, the 5'LTR of this vector would be of the same genome as the env gene (i.e. from the same source). Such a vector could be used instead of an SIV env packaging-defective vector, to create virions. By such a change, the resultant vector systems may be used in a wider host range or may be restricted to a smaller host range. For example, an envelope protein from vesicular stomatitis virus or rabies virus may be used to make the vector tropic for many different cell types.

Any suitable cell line may be used in methods of the invention. Preferably, a mammalian cell line is used, for example CV-1, Hela, Raji, SW480 or CHO.

In order to increase production of the viral cellular products, a promoter other than the 5' LTR may be used, for example the 5' LTR may be replaced with a promoter that will preferentially express genes in CV-1 or HeLa cells. A suitable promoter can easily be determined by the person of ordinary skill in the art depending on the cell line used.

In order to enhance the level of viral cellular products, enhancer sequences may be added to the vector to increase the activity of the LTR and/or promoter. Suitable enhancer sequences can readily be determined by a person of ordinary skill in the art depending on the host cell line.

By using a series of vectors that together contain a complete retroviral genome (though a combination of HIV-2 and SIV sequences), cell lines may be produced that produce a virion that is identical to the SIV virion except that the virion does not contain SIV RNA. These virions are readily obtained from the cells. For example, the cells may be cultured and the supernatant harvested. Depending on the desired use, the supernatant containing the virions may be used directly or the virions may be separated, isolated and/or purified from the supernatant by standard techniques such as gradient centrifugation, filtering etc.

Attenuated virions as described herein may be extremely useful in preparing a vaccine. The virions may be used to generate an antibody response to these virions. Pseudotyped virions produced from cell lines co-transfected with retroviral gag/pol and protease genes and containing the env gene from another virus may be useful in creating a vaccine against this other virus.

Methods of Mutation

Mutations may be made in HIV-2 or SIV by homologous recombination methods well known to those skilled in the art. For example, HIV-2 or SIV genomic RNA may be transfected together with a vector, preferably a plasmid vector, comprising the mutated sequence flanked by homologous HIV-2 or SIV sequences. The mutated sequence may comprise deletions, insertions or substitutions, all of which may be constructed by routine techniques. Insertions may include selectable marker genes, for example lacZ, for screening recombinant viruses by, for example, β-galactosidase activity.

The number of bases that need to be deleted or mutated can vary greatly. For example, in SIV, the deletion of the 85-base pair sequence of SEQ ID NO: 2 is sufficient to result in loss of packaging ability. However, even smaller deletions in this region may also result in loss of packaging efficiency. A deletion as small as about 5, 10, 15, 20, 30, 40, 50, 60, 70 or 80 bases in this region may remove efficient packaging ability. The mutation may comprise deletion or modification of a fragment of SEQ ID NO: 2 or a variant thereof of 5 or more nucleotides in length. Such a fragment is preferably an internal fragment, that is to say, a deletion of 5 or more nucleotides within SEQ ID NO: 2, not including the end nucleotides of SEQ ID NO: 2. Alternatively, larger deletions may be incorporated as described above. The size of a particular deletion can readily be determined by the person of ordinary skill in the art.

Essential genes may be rendered functionally inactive by several techniques well known in the art. For example, they may be rendered functionally inactive by deletions, substitutions or insertions, preferably by deletions. Deletions may remove portions of the genes or the entire gene. For example, deletion of only one nucleotide may be made, resulting in a frame shift. However, larger deletions are generally preferred, for example at least 25%, more preferably at least 50% of the total coding and non-coding sequence (or alternatively, in absolute terms, at least 10 nucleotides, more preferably at least 100 nucleotides, most preferably, at least 1000 nucleotides). It is particularly preferred to remove the entire gene and some of the flanking sequences. Inserted sequences may include the heterologous genes described below.

Those skilled in the art are well able to construct vectors as described herein. For further details see, for example, *Molecular Cloning: a Laboratory Manual:* 3rd edition, Sambrook & Russell, 2001, Cold Spring Harbor Laboratory Press.

Many known techniques and protocols for manipulation of nucleic acid, for example in preparation of nucleic acid constructs, mutagenesis, sequencing, introduction of DNA into cells and gene expression, and analysis of proteins, are described in detail in *Protocols in Molecular Biology*, Second Edition, Ausubel et al. eds. John Wiley & Sons, 1992.

Heterologous Genes and Promoters

A vector or virus may be modified to carry a heterologous gene, that is to say a gene or nucleic acid coding sequence other than one present in the HIV-2 or SIV genome. In particular, vectors are provided which have HIV-2 derived sequences sufficient to allow packaging of the vector into a SIV capsid. The vectors may be derived from HIV-2 genomes, incorporating mutations or deletions in one or more HIV-2 genes, or may be derived from other expression vectors which are modified to incorporate HIV-2 packaging sequences.

The term "heterologous gene" comprises any gene or nucleic acid coding sequence other than one present in the HIV-2 genome. The heterologous gene may be any allelic variant of a wild-type gene, or it may be a mutant gene. The term "gene" is intended to cover nucleic acid sequences encoding a polypeptide and nucleic acid sequences which are capable of being at least transcribed. Thus, sequences encoding mRNA, tRNA and rRNA are included within this definition. The sequences may be in the sense or antisense orientation with respect to the promoter. Antisense constructs can be used to inhibit the expression of a gene in a cell according to well-known techniques. Sequences encoding mRNA will optionally include some or all of 5' and/or 3' transcribed but untranslated flanking sequences naturally, or otherwise, associated with the translated coding sequence. It may optionally further include the associated transcriptional control sequences normally associated with the transcribed sequences, for example transcriptional stop signals, polyadenylation sites and downstream enhancer elements.

The heterologous gene may be inserted into for example an HIV-2 vector by homologous recombination of HIV-2 strains with, for example, plasmid vectors carrying the heterologous gene flanked by HIV-2 sequences. The heterologous gene may be introduced into a suitable plasmid vector comprising HIV-2 sequences using cloning techniques well-known in the art. The heterologous gene may be inserted into an HIV-2 vector at any location. It is preferred that the heterologous gene is inserted into an essential HIV-2 gene. Preferably the vector is derived from an HIV-2 genome, but includes deletion of one, two or several of the HIV-2 genes, up to the minimal sequences of the HIV-2 genome to provide for packaging and expression of the heterologous gene.

The transcribed sequence of the heterologous gene is preferably operably linked to a control sequence permitting expression of the heterologous gene in mammalian cells. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

A control sequence may comprise a promoter allowing expression of the heterologous gene and a signal for termination of transcription. The promoter may be selected from promoters which are functional in mammalian, preferably human, cells. The promoter may be derived from promoter sequences of eukaryotic genes. For example, it may be a promoter derived from the genome of a cell in which expression of the heterologous gene is to occur. With respect to eukaryotic promoters, they may be promoters that function in a ubiquitous manner (such as promoters of β-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter or promoters of HIV-2 genes.

The HIV-2 LTR promoter or promoters containing elements of the LTR promoter, are especially preferred. The expression cassette may further comprise a second promoter and a second heterologous gene operably linked in that order and in the opposite or same orientation to the first promoter and first heterologous gene wherein said second promoter and second heterologous gene are the same as or different to the first promoter and first heterologous gene. Thus a pair of promoter/heterologous gene constructs may allow the expression of pairs of heterologous genes, which may be the same or different, driven by the same or different promoters. Furthermore, the product of the first heterologous gene may regulate the expression of the second heterologous gene (or vice-versa) under suitable physiological conditions.

The expression cassette can be constructed using routine cloning techniques known to persons skilled in the art (see, for example, Sambrook et al., 1989, Molecular Cloning—a laboratory manual; Cold Spring Harbor Press).

It may also be advantageous for the promoters to be inducible so that the levels of expression of the heterologous gene can be regulated during the lifetime of the cell. Inducible means that the levels of expression obtained using the promoter can be regulated. For example, in embodiments in which more than one heterologous gene is inserted into the vector or HIV-2 genome, one promoter may comprise a promoter responsive to the expression of the second protein and driving the heterologous gene the expression of which is to be regulated. The second promoter may comprise a strong promoter (e.g. the CMV IE promoter) driving the expression of the second protein.

In addition, any of these promoters may be modified by the addition of further regulatory sequences, for example enhancer sequences. Chimeric promoters may also be used comprising sequence elements from two or more different promoters described above, for example an MMLV LTR/HIV-2 fusion promoter.

The heterologous gene may encode any desired protein. The heterologous gene may encode, for example, proteins involved in the regulation of cell division, for example mitogenic growth factors, cytokines (such as α-, β- or γ-interferon, interleukins including IL-1, IL-2, tumour necrosis factor, or insulin-like growth factors I or II), protein kinases (such as MAP kinase), protein phosphatases and cellular receptors for any of the above.

The heterologous gene may encode enzymes involved in cellular metabolic pathways, for example enzymes involved in amino acid biosynthesis or degradation (such as tyrosine hydroxylase), or proteins involved in the regulation of such pathways, for example protein kinases and phosphatases. The heterologous gene may encode transcription factors or proteins involved in their regulation, membrane proteins (such as rhodopsin), structural proteins (such as dystrophin) or heat shock proteins such as hsp27, hsp65, hsp70 and hsp90.

Preferably, the heterologous gene encodes a polypeptide of therapeutic use, or whose function or lack of function may be important in a disease process. For example, tyrosine hydroxylase may be useful in the treatment of Parkinson's disease, rhodopsin may be useful in the treatment of eye disorders, dystrophin may be useful to treat muscular dystrophy, and heat shock proteins may be useful in the treatment of disorders of the heart and brain associated with ischaemic stress. Polypeptides of therapeutic use may include cytotoxic polypeptides such as ricin, or enzymes capable of converting a precursor prodrug into a cytotoxic compound for use in, for example, methods of virus-directed enzyme prodrug therapy or gene-directed enzyme prodrug therapy. In the latter case, it may be desirable to ensure that the enzyme has a suitable signal sequence for directing it to the cell surface, preferably a signal sequence that allows the enzyme to be exposed on the exterior of the cell surface whilst remaining anchored to cell membrane. Suitable signal sequences are well known in the art.

A heterologous gene may encode an antigenic polypeptide useful as a vaccine. Preferably such antigenic polypeptides are derived from pathogenic organisms, for example bacteria or viruses, or from tumours.

A heterologous gene may include a marker gene (for example encoding β-galactosidase, luciferase or green fluorescent protein) or a gene whose product regulates the expression of other genes (for example, transcriptional regulatory factors.

Gene therapy and other therapeutic applications may well require the administration of multiple genes using the methods described herein. The expression of multiple genes may be advantageous for the treatment of a variety of conditions.

Nucleic acid, vectors, viruses and host cells as described herein may be provided as part of a kit, e.g. in a suitable container such as a vial in which the contents are protected from the external environment. The kit may include instructions for use, e.g. a method of producing a chimeric virus, for example in vitro or in vivo. A kit may include one or more other reagents required, such as buffer solutions, carriers, etc. Reagents may be provided within containers which protect them from the external environment, such as a sealed vial. A kit may include instructions for use.

Administration

The vectors, host cells and viruses described herein may be used to deliver therapeutic genes to a human or animal in need of treatment.

A therapeutic gene may for example be inserted into a vector as described above. Subsequently, host cells may be co-transfected in vitro with a vector comprising the heterologous gene and the HIV-2 packaging sequences and a packaging defective SIV vector. Culturing the cells leads to production of SIV viral capsids, into which the heterologous gene vectors are packaged through the HIV-2 packaging sequences. The resultant recombinant virus may, optionally, be purified and/or isolated before use.

In other embodiments, the host cell may be co-transfected in vitro and then administered to an individual, for example a mammal, in particular a primate such as a human. The host cell may then produce viral particles comprising heterologous nucleic acid in situ, as described herein.

In other embodiments, target cells may be co-transfected with the first and second vectors in vivo. The target cells within the body of the individual then produce viral particles in situ, as described herein.

While it is possible for the vectors, viruses or host cells to be administered alone, it is preferable to present it as a pharmaceutical composition (e.g., formulation) comprising at least one active compound, as defined above, together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents. Vaccine compositions, in which the heterologous gene encodes an antigenic peptide or protein may be formulated with adjuvants to enhance the immune response generated.

The term "pharmaceutically acceptable" as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Suitable carriers, excipients, etc. can be found in standard pharmaceutical texts, for example, Remington's Pharmaceutical Sciences, 18th edition, Mack Publishing Company, Easton, Pa., 1990.

The formulations may conveniently be presented in unit dosage form and may be prepared by any methods well known in the art of pharmacy. Such methods include the step of bringing the active compound into association with a carrier which may constitute one or more accessory ingredients. In general, the formulations are prepared by uniformly and intimately bringing into association the active compound with liquid carriers or finely divided solid carriers or both, and then if necessary shaping the product.

The pharmaceutical composition may be administered to an individual in such a way that the virus containing the therapeutic gene for gene therapy can be incorporated into cells at an appropriate region of the body.

The composition may, for example, be formulated for parenteral, intramuscular, intravenous, subcutaneous, intraocular or transdermal administration.

Formulations suitable for parenteral administration (e.g., by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilisers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

It will be appreciated that appropriate dosages of the vectors, viruses or host cells, and compositions comprising vectors, viruses or host cells, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Typically, the amount of virus administered is in the range of from $10^4$ to $10^{10}$ pfu, preferably from $10^5$ to $10^8$ pfu, more preferably about $10^6$ to $10^7$ pfu. When injected, typically 1 to 10 μl of virus in a pharmaceutically acceptable suitable carrier or diluent is administered.

Assay Methodologies

Viruses produced as described herein may also be used in methods of scientific research. Thus, other aspects of the invention relate to methods of assaying gene function in mammalian cells, either in vitro or in vivo. A method of determining the function of a heterologous gene may comprise:

(a) producing virus particles comprising an SIV capsid and a vector having a heterologous gene packaged via HIV-2 packaging signals,
(b) introducing the resulting virus into a mammalian cell line; and,
(c) determining the effect of expression of said heterologous gene in said mammalian cell-line.

For example, the cell-line may have a temperature-sensitive defect in cell division. When an HIV-2 strain comprising a heterolpgous gene is introduced into the defective cell-line and the cell-line grown at the restrictive temperature, a skilled person will easily be able to determine whether the heterologous gene can complement the defect in cell division. Similarly, other known techniques can be applied to determine if expression of the heterologous gene can correct an observable mutant phenotype in the mammalian cell-line.

This procedure can also be used to carry out systematic mutagenesis of a heterologous gene to ascertain which regions of the protein encoded by the gene are involved in restoring the mutant phenotype.

Similar methods may be used in animals, for example mice, carrying so-called "gene knock-outs". A wild-type heterologous gene may be introduced into the animal using a mutant HIV-2 strain as described herein and the effect on the animal determined using various behavioural, histochemical or biochemical assays known in the art. Alternatively, a mutant heterologous gene may be introduced into either a wild-type or "gene knock-out" animal to determine if disease-associated pathology is induced. In other embodiments, an antisense nucleotide may be introduced using the virus particle of the invention to create in effect a knock-out animal.

Alternatively, the mutant HIV-2 virus of the invention may be used to obtain expression of a gene under investigation in a target cell with subsequent incubation with a test substance to monitor the effect of the test substance on the target gene.

Thus, the methods described herein may be useful for the functional study of genes implicated in disease.

Various further aspects and embodiments of the present invention will be apparent to those skilled in the art in view of the present disclosure. All documents mentioned in this specification are incorporated herein by reference in their entirety.

The invention encompasses each and every combination and sub-combination of the features that are described above.

Certain aspects and embodiments of the invention will now be illustrated by way of example and with reference to the figures described above and tables described below.

Table 1 shows a summary of results of virion RNA PCR for GFP and FACS data on transduced cells with cross-packaged lentiviral vectors Table 2 shows the cross packaging efficiency of HIV-1 gag-pol (see FIG. 1).

Figure 2:
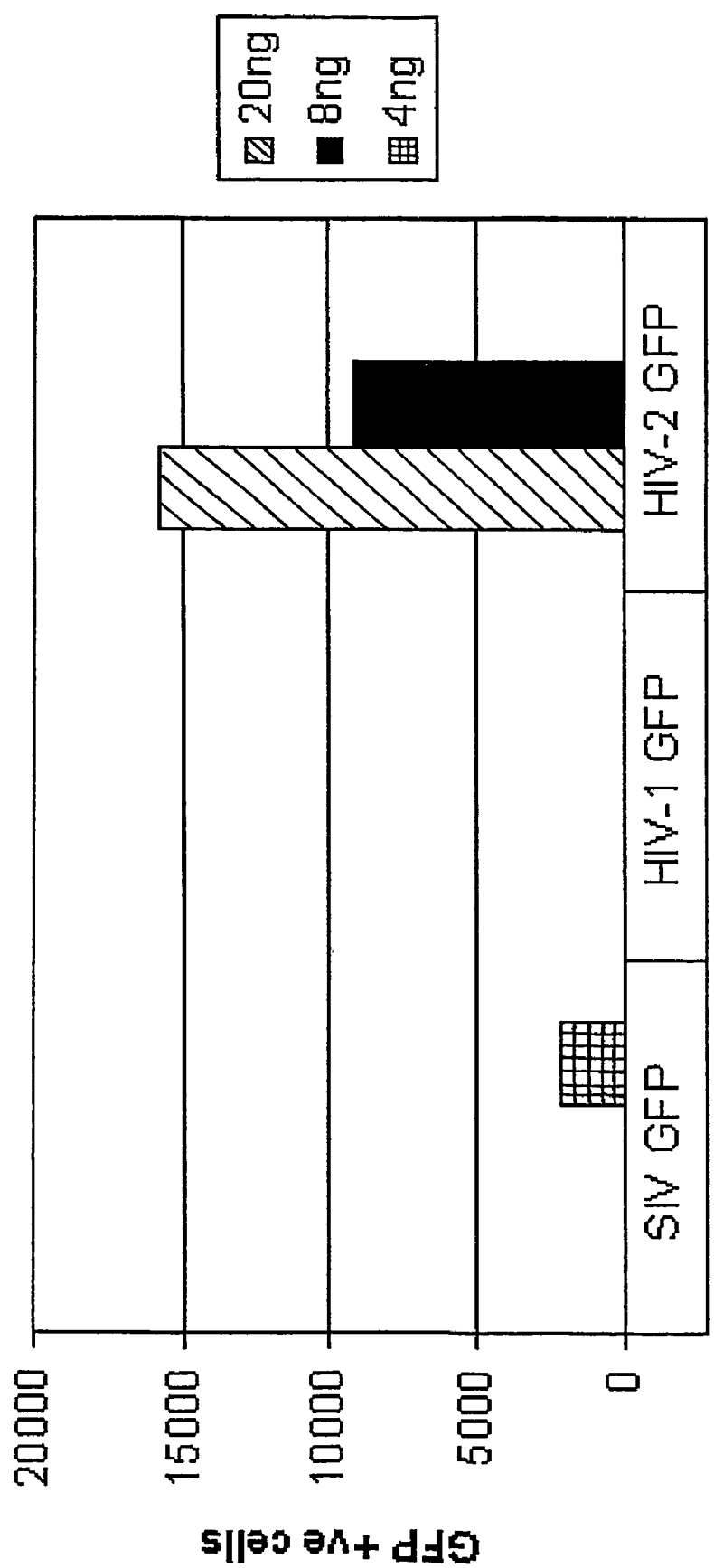
FIG. 2 shows the cross packaging efficiency of SIV gag-pol (see table 3).

Table 3 shows the cross packaging efficiency of SIV gag-pol (see FIG. 2).

Figure 3:
FIG. 3 shows the cross packaging efficiency of HIV-2 gag-pol (see table 4).
Figure 4:
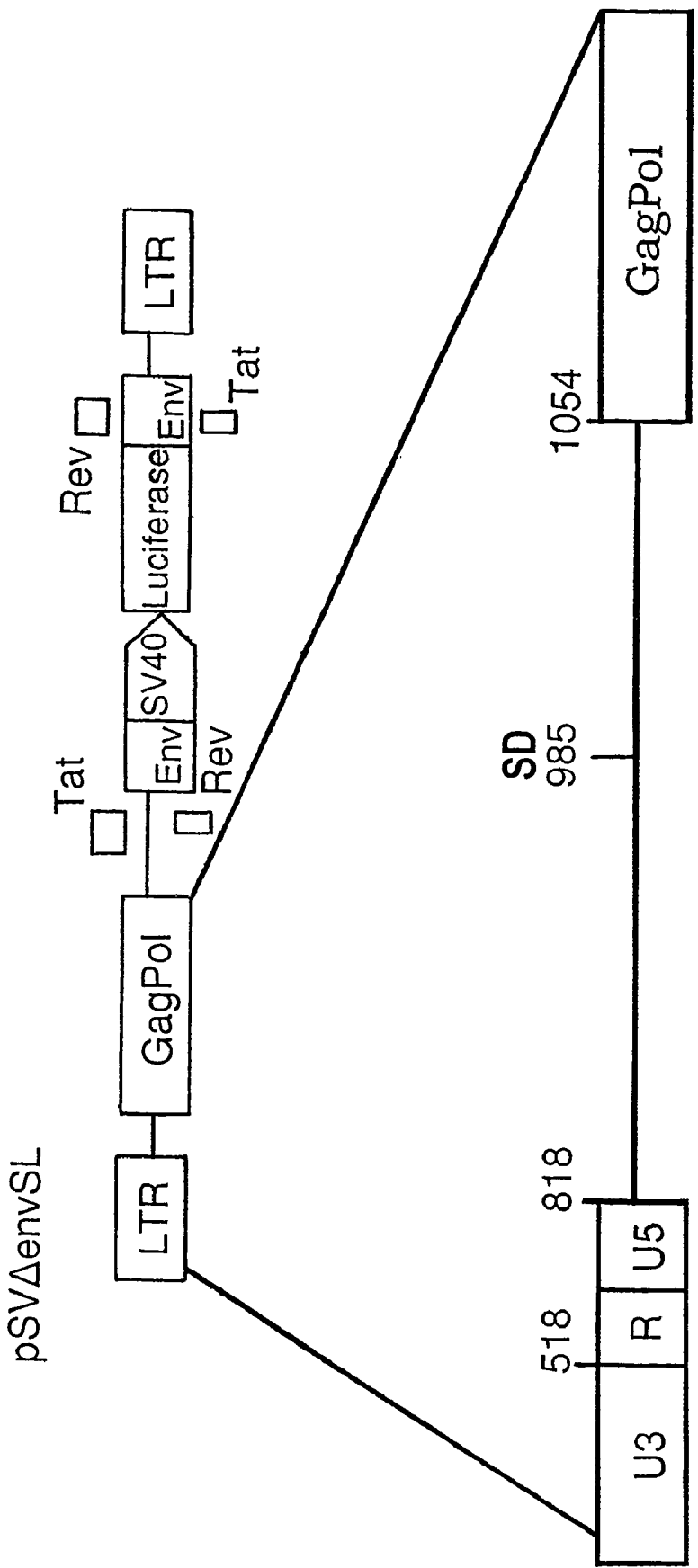
FIG. 4 shows the SIVmac leader region.
Figure 5:
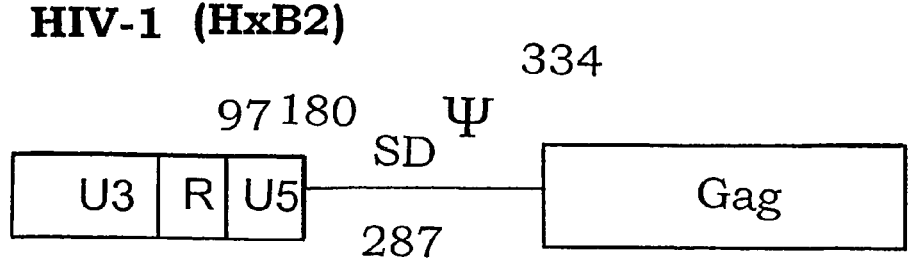
FIG. 5 shows a comparison of HIV-1, HIV-2 and SIV leader sequence regions with localization of the major packaging signal. Numbering is from RNA cap size and not the 5' LTR.
Figure 5:
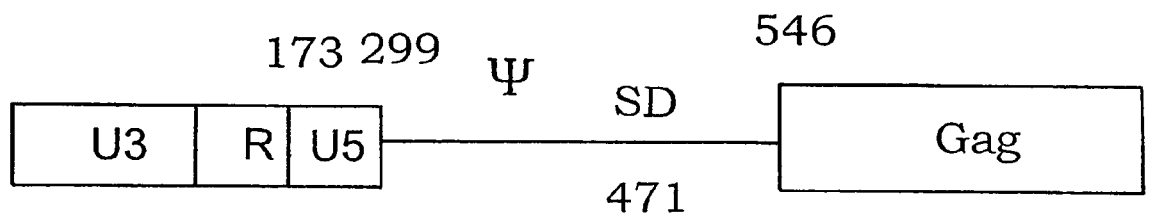
Figure 5:
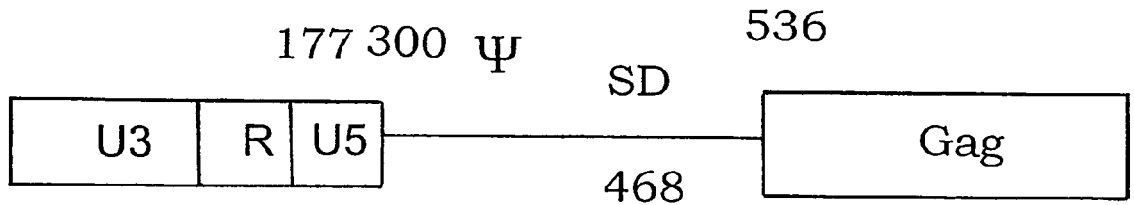

Table 4 shows the cross packaging efficiency of HIV-2 gag-pol (see FIG. 3).

Table 5 shows examples of genomic sequences of SIV strains.

Table 6 shows examples of genomic sequences of HIV-2 strains

EXPERIMENTAL

Overview

The experiments set out below show that HIV-2 helper sequences do not package SIV vectors but SIV helper sequences do package HIV-2 vectors. Helper sequences derived from SIV are shown to enable the packaging of HIV-2 RNA at high levels and permit efficient gene transfer by the packaged HIV-2 vectors.

Lentiviral Vectors

All SIV constructs are based on the SIV isolate SIVmac32H (Genbank D01065). Numbering refers to positions in the retroviral genome, where position 1 is the first base of the 5' LTR.

The constructs based on HIV-1 and SIV have been previously described (Kaye et al (1998), Strappe et al (2003)). The HIV-1 gene transfer vector HR'GFP was modified to include the HIV-1 central polypurine tract or DNA flap sequence. The sequence was PCR amplified and cloned into the unique Clal site upstream of the RRE sequence. The HIV-2 gene transfer vector was also modified from the original construct by replacing the SV40-Puromycin construct with a CMV-GFP reporter gene construct (McCann and Lever (1997)). The HIV-2 Gag-Pol construct contains a deletion in the 5' untranslated region, which has been shown to abrogate packaging. (Griffin (2001))

Lentiviral Vector Production

Lentiviral vectors were produced by calcium phosphate transfection of 293T cells grown in DMEM media and 10% FCS with 7 ug of the gene transfer vector, 7 ug of the Gag-Pol construct, 3 ug of the Rev expresser and 3 ug of the VSV-G heterologous envelope. For HIV-2 and SIV vector production, the Rev expressor was omitted. 24 hours following transfection the media was replaced and supernatant containing recombinant virions was recovered 48 hours post transfection. Virions were concentrated by ultracenrifugation for 2.5 hours at 25,000 RPM in an SW28 Beckmann rotor. The viral pellet was resuspended in 300 ul of tissue culture media, aliquoted and stored at −70° C.

Lentiviral vectors were titered using a commercially available RT-assay (Cavid Tech, Uppsala) Vector preparations were measured in duplicate and normalised to a concentration of 8 ng of RT per μl.

Levels of RNA packaging were assessed by RT-PCR of virion associated RNA. Virion RNA was extracted using the Qiagen Viramp kit from 10 ng of virus (RT levels). Following extraction, the RNA was treated with RNase free DNase for 10 mins at 37° C. and the DNase then inactivated by incubation at 70° C. for a further 10 mins. An aliquot of RNA was reverse transcribed to cDNA using the Promega Improm RT system with an antisense GFP primer. The cDNA was then serially diluted (1:10) and each dilution amplified using sense and antisense primers to GFP. Amplified products were resolved by agarose gel electrophoresis and EtBR staining.

The transduction efficiency of cross-packaged vectors was assessed by FACS analysis of GFP positive cells. A range of viral vector concentrations from 40 ng to 4 ng was used to transduce $1\times10^6$ SV2C cells in a six well plate. Viral vector was diluted in DMEM containing 6 ug/ml polybrene and cells were exposed to virus for 5 hours. The media was then replaced and GFP expression was assessed at time periods after 72 hours post-transduction

Glial Cell Culture and Stem Cell Culture

Primary mixed glial cultures were prepared from the brains of newborn rats>3 days old as previously described. Mixed glial cultures were derived from these cells, once they were confluent, by trypsinisation. The cells were then resuspended in DMEM containing 10% FCS and 1% PSF and centrifuged at 10,000 RPM for 5 minutes. The supernatant was removed and cells were resuspended in DMEM/10% FCS and plated onto Poly-D-Lysine coated coverslips in 24 well plates. Transduction of glial cultures with lentiviral vectors was carried out as described for SV2C cultures. 72 hours post transduction, glial cultures were fixed in 4% paraformaldehyde and stored in PBS at 4° C. prior to immunostaining.

Embryonic neuronal stem cell culture was performed as described previously (Wright et al (2003)). Transduction of Stem cell cultures was performed with 10 ng of viral vector in stem cell media for 4 hours, followed by replacement of the media. 72 hours post transduction, the cell were fixed in 4% paraformaldehyde, followed by immunostaining for GFP, GFAP and Tubulin.

Immunostaining

Lentiviral vector transduced mixed glial cultures were first blocked using 3% goat serum in TXTBS (0.2% triton X-100, in Tris Buffered Saline) for one hour. Monoclonal anti GFAP (Sigma, 1:500) and polyclonal goat anti rabbit GFP (Molecular Probes), 1:1000) were diluted in TXTBS with 1% normal goat serum (NGS) for 2 hours. Cells were then washed in TBS for 3×10 minutes. Cells were then incubated with secondary antibodies, goat anti mouse Alexa (Molecular Probes, 1:500) and biotinylated goat anti rabbit (Amersham Biosciences, 1:500) for 90 minutes. Following a second 3×10 minute wash in TBS, Streptavidin-FITC (Serotec, 1:100) was added in TBS with 1% NGS and Bis-benzamide (Sigma, 1:5000). Coverslips were then mounted in Fluorosave reagent (Calbiochem). Cell counts of immunostained mixed glial cultures were performed from one edge of the coverslip all the way across to the other, horizontally and vertically. A 0.5 $mm^2$ area was counted every 1.5 mm.

Cross-Packaging of Lentiviral RNA Following concentration of viral vectors by ultracentrifugation, viral vector titre was assessed by the reverse transcriptase assay, which gives a quantitative measure of RT in ng. The concentration of each viral vector was normalised to 4 ng/ul following previous optimisation. The levels of RNA packaged in virions were assessed by RT-PCR of the packaged GFP transgene using specific primers. Virion extracted RNA was reverse transcribed to cDNA and diluted serially to 1/10, 1/20 and 1/40 and then amplified by PCR. Electrophoresis of PCR products reveals a limit of positivity and signal strength. HIV-1 Gag-Pol was found to efficiently package HIV-1 RNA and can also cross package HIV-2 vector RNA at similar levels, both to a limiting dilution of 1/20. In comparison, cross packaging of SIV vector RNA by HIV-1 Gag-Pol is reduced and is similar to levels of SIV vector RNA packaged by SIV Gag-Pol to a limiting dilution of 1/10.

SIV Gag-Pol was found to efficiently cross package HIV-2 vector RNA to a limiting dilution of 1/40, which is greater than the SIV homologous vector system (1/10) and SIV Gag-pol+HIV-GFP vector system (1/10). The ability of HIV-2 Gag-Pol to cross package HIV-1 and SIV vector RNA is significantly reduced compared to the homologous HIV-2 system which showed similar levels of packaged RNA to the HIV-1 homologous vector system.

Gene Transfer Efficiency of Cross Packaged Vectors

To investigate the gene transfer efficiency of cross-packaged vectors, SVC2 cells were transduced with a range of vector-virion preparations at differing concentrations as measured by RT-assay. FIGS. 1 to 3 shows a series of FACS plots of GFP positive cells following transduction with viral vector and this data is also described in tables 2 to 4.

HIV-1 Gag-Pol was used to package two separate HIV-1 vectors (+/−cPPT sequence), the gene transfer vector containing the cPPT demonstrated an increased transduction rate of SVC2 cells up to almost a two fold increase with an input viral vector of 10 ng (FIG. 1; table 2). Transfer of 20 ng of an HIV-2 vector packaged by HIV-1 Gag-Pol showed a similar transduction efficiency to that of the HIV-1 cPPT vector packaged by HIV-1 Gag-Pol, suggesting that the HIV-2 cPPT region also contributed to increased transduction. Transfer of an SIV vector expressing GFP, cross-packaged by HIV-1 Gag-Pol was significantly (almost six fold) lower compared to the homologous HIV-1 viral vector (−cPPT). This may reflect a low productivity in the SIV vector system, however the gene transfer efficiency of the homologous SIV vector (FIG. 2; table 3) was similar to HIV-1 using 4 ng of RT. SIV Gag-Pol demonstrated the ability to cross package and transfer a HIV-2 GFP vector at levels slightly higher than the homologous HIV-1 vector system. This is in contrast to the lack of gene transfer of a HIV-1 vector packaged by SIV Gag-Pol. The levels of HIV-2 vector RNA packaged by SIV Gag-Pol (FIG. 2; table 3) are also reflected in the high gene transfer efficiency. This packaging relationship between SIV and HIV-2 would appear to be non-reciprocal, with lower amounts of SIV vector RNA packaged by the HIV-2 Gag-Pol (FIG. 3, table 4) and no evidence of any significant gene transfer. Comparing the HIV-1 and HIV-2 homologous vector systems showed that levels of gene transfer to SVC2 cells were slightly higher for HIV-2 compared to a cPPT negative HIV-1 vector but lower when compared to the HIV-1 vector containing the cPPT region. HIV-2 Gag-Pol would appear to have no ability to cross-package and transfer HIV-1 vector, which is similar to a previous study (Kaye and Lever, 1998) with no significant transduction of SVC2 cells.

Transduction of CNS Cell Types

The cross-packaging and gene transfer relationship between SIV Gag-Pol and a HIV-2 vector was verified by transducing rat primary mixed glial cultures. The cultures were transduced with either 40 ng or 20 ng of viral vector and the efficiency of transduction compared to that achieved with HIV-1 and HIV-2 homologous vector systems. Cells were immunostained for GFP expression and the astrocyte marker GFAP, and counted.

Transducing the glial cultures with 20 ng of a SIV Gag-Pol+HIV-2 GFP viral vector resulted in GFP positivity in over 30% of cells; approximately 80% of these positive cells were astrocytes. A similar transduction rate was seen with the HIV-1 homologous vector system, which lacks the cPPT sequence, using 20 ng of viral vector. At the same viral vector concentration, the HIV-2 homologous vector system transduced approximately 25% of glial cells with 62% of these cells staining for GFAP. The effect of the cPPT sequence on HIV-1 viral vector transduction is evident with over 60% of glial cell expressing GFP with 20 ng of input vector and approximately 58% with long of vector. In summary, the gene transfer efficiency of the HIV-2 GFP vector cross packaged by SIV Gag-Pol to glial cells was similar to both the HIV-1 and HIV-2 homologous vector systems (see table 1).

Transduction of human embryonic neuronal stem cells was also performed using the HIV-1 and HIV-2 homologous vector system and with the SIV Gag-Pol/HIV-2 GFP. The transduction efficiency was assessed qualitatively by fluorescence microscopy using 20 ng of viral vector, and the SIV Gag-Pol/HIV-2 GFP cross packaged vector system were found to transduce both astrocytes and neurons post differentiation as demonstrated by immunostaining with GFAP (astrocytes) and beta-tubulin (Neurons). The cross-packaged vector system performed as well as the HIV-1 and HIV-2 homologous vector systems with astrocytes being transduced at a slightly higher efficiency.

In conclusion, a non-reciprocal cross packaging relationship between SIV and HIV-2 has been identified herein. The SIV Gag-Pol/HIV-2 vector combination demonstrated equivalent transduction efficiencies in 293T cells, rat primary astrocytes and embryonic stem cells to that of homologous HIV-1 and HIV-2 vector systems.

The methods described herein combine the safety of a vector system in which helper and vector sequences are derived from two different viruses (resulting in very low probability of recombination); with the general advantages of lentiviral vectors and the specific advantages of HIV-2 and SIV sequences. The methods are shown to have a transduction efficiency comparable to the best of other lentiviral systems.

Animal models based on asian macaques and baboons exist for SIV and HIV-2. Thus the SIV/HIV-2 chaemeric vectors described herein may be subjected to direct biosafety testing in animals and subsequently usage in human studies.

REFERENCES

Trono D. Gene Therapy 2000, 7, 20-23.
Connolly JB Gene Therapy 2002, 9, 1730-1734.
Zufferey R et al. Nat Biotechnol 1997, 871-875.
Naldini L et al. Science 1996, 272, 263-267.
Blomer U et al. J Virol 1997, 71, 6641-6649.
Kordower JH et al. Science 2000, 290, 767-773.
Dull et al. J Virol, 1998, 72, 8463-8471.
Lever A et al, J Virol 1989, 63, 4085-4087.
McCann E. M et al. J Virol, 1997, 71, 4133-4137.
Strappe P M et al. J Gen Virol, 2003, 84, 2423-2430.
Kemler I et al. J Virol, 2002, 76, 11889-11903.

Browning M T et al. J Gen Virol, 2003, 84, 621-627.
Griffin et al. J Virol 2001, 75, 12058-12069
Kaye, JF and Lever, AML. J Virol, 1998, 72, 5877-5885.
White et al. J Virol, 1999, 73, 2832-2840.
Wright et al J Neurochem. 2003 July; 86(1):179-950
Rizvi, TA and Panganibian, A. T (1993) J. Virol, 67, 2681-2688.
Browning et al (2001) J Virol. 75, 5129-5140.
Goujon et al (2003) J Virol, 77, 9295-9340.
Sastry L et al (2003) Mol Ther. 2003; 8:830-9.
Escarpe P et al Mol Ther. 2003, 8:332-41.
Zhao C et al Glia. 2003, 42:59-67.
Baekelandt V et al Gene Ther. 2003, 10:1933-40.
Ruitenberg MJ et al Neurobiol Dis. 2004, 15, 394-406.
Ostenfeld T et al J Neurosci Res. 2002, 69, 955-65.
Certo J L, et al (1998). J. Virol, 72, 5408-5413.
McCann, E. M and Lever A. M (1997) J virol. 71, 4133-4137.
Properzi F and Fawcett J W (2004) News physiol Sci, 19, 33-38.
Tai et al (2004) Curr Opin Pharmacol. 2004, 4, 98-104.
Englund U et al (2000) Neuroreport. 2000, 11, 3973-7.
Manganini M et al (2002) Hum Gene Ther, 13:1793-807.
Zennou V et al (2001)

TABLE 1

| Gag-Pol | Gene Transfer Vector (GFP) | RNA Packaged (Limit of RT-PCR) | GFP expression (Transduced cells) |
|---|---|---|---|
| HIV-1 | HIV-1 | $10^3$ | +++ |
| HIV-1 | HIV-1 (+cPPT) | | ++++ |
| HIV-1 | HIV-2 | $10^3$ | +++ |
| HIV-1 | SIV | $10^2$ | + |
| SIV | SIV | $10^2$ | + |
| SIV | HIV-1 | $10^2$ | −(neg) |
| SIV | HIV-2 | $10^4$ | ++++ |
| HIV-2 | HIV-2 | $10^3$ | +++ |
| HIV-2 | HIV-1 | $10^2$ | −(neg) |
| HIV-2 | SIV | $10^2$ | −(neg) |

TABLE 2

| | HIV-1 GFP | HIV-1 GFP (+cPPT) | HIV-2 GFP | SIV GFP |
|---|---|---|---|---|
| 40 ng | 13770 | 21362 | 23077 | |
| 20 ng | 6104 | 12594 | 11505 | |
| 8 ng | 2122 | 5639 | | |
| 4 ng | 1895 | 5852 | | 394 |

TABLE 3

| | SIV GFP | HIV-1 GFP | HIV-2 GFP |
|---|---|---|---|
| 20 ng | 0 | 0 | 15792 |
| 8 ng | 0 | 0 | 9232 |
| 4 ng | 2152 | 14 | 0 |

TABLE 4

| | HIV-2 GFP | HIV-1 GFP | SIV GFP |
|---|---|---|---|
| 20 ng | 9621 | | |
| 8 ng | 4094 | | |
| 4 ng | 1443 | 40 | 16 |

TABLE 5

| SIV clone/strain | Acc No | GI number |
|---|---|---|
| SIVagmSAB-1 | U04005.1 | gi466229 |
| — | M58410.1 | gi334422 |
| clone 4.41 | M31325.1 | gi334753 |
| — | M32741.1 | gi334692 |
| isolate STM | M83293.1 | gi334799 |
| | M29975.1 | gi1220519 |
| clone 1.5 | L03295.1 | gi334763 |
| SIVMne027 | U79412.1 | gi2737927 |
| SIVsmE543 | U72748.1 | gi1695908 |
| SIVtan | U58991.1 | gi1929498 |
| smmPGm | AF077017.1 | gi3462587 |
| SIVlhoest | AF075269.1 | gi3342102 |
| US | AF103818.1 | gi4336706 |
| | AF131870.1 | gi5106562 |
| SIVcpz | AF115393.1 | gi6594657 |
| 239 | M33262.1 | gi334647 |
| SIVCPZ | AJ271369.1 | gi8920373 |
| | L06042.1 | gi294960 |
| Mm251 | M19499.1 | gi334657 |
| H328 | AF316141.1 | gi11612154 |
| SIVcolCGU1 | AF301156.1 | gi12657808 |
| 1A11 | M76764.1 | gi334170 |
| | M66437.1 | gi334433 |
| SIVmnd14cg | AF328295.1 | gi15055096 |
| SIVsmSL92b | AF334679.1 | gi14164886 |
| | M27470.1 | gi334683 |
| SIVgsn-99CM71 | AF468658.1 | gi22037883 |
| SIVgsn-99CM166 | AF468659.1 | gi22037893 |
| | M30931.1 | gi334400 |
| SIVmnd-2 | AF367411.2 | gi26557006 |
| SIVcpzTAN1 | AF447763.1 | gi27448793 |
| SIVdrl1FAO | AY159321.1 | gi29367069 |
| SIVmnd5440 | AY159322.1 | gi29367079 |
| SIVmus-01CM1085 | AY340700.1 | gi37728000 |
| SIVmon-99CMCML1 | AY340701.1 | gi37728010 |
| SIVden | AJ580407.1 | gi39930157 |
| | NC_004455.1 | gi27311166 |
| | NC_001549.1 | Gi9627204 |
| | AF382829.1 | Gi21105238 |

TABLE 6

| HIV-2 strain/clone | Acc Number | GI number |
|---|---|---|
| 96FR12034 | AY530889.1 | gi47680175 |
| | NC_001722.1 | gi9628880 |
| MCR35 | AY509260.1 | gi41056785 |
| MCN13 | AY509259.1 | gi41056775 |
| 01JP-IMCJ/KR020.1 | AB100245.1 | gi32879750 |
| BEN | M30502.1 | gi1332355 |
| 7312a | L36874.1 | gi16905444 |
| | J04542.1 | gi325654 |
| ALI | AF082339.1 | gi4007991 |
| EHO | U27200.1 | gi995584 |
| | D00835.1 | gi3153166 |
| D205 | X61240.1 | gi60256 |
| | U38293.1 | gi1845204 |
| | M31113.1 | gi1339798 |
| ROD | M15390.1 | gi1332361 |
| SBLISY | J04498.1 | gi1332357 |
| SBL-6699-85 | A05350.1 | gi345067 |
| | U22047.1 | gi747644 |
| 2UC1 | L07625.1 | gi325762 |
| GH-1 | M30895.1 | gi325709 |

The invention claimed is:

1. A method of expressing a therapeutic or an antigenic protein or peptide in an individual, the method comprising:
   administering to the individual an effective amount of a chimeric virus comprising a heterologous nucleic acid sequence encoding the therapeutic or the antigenic protein or peptide, or a pharmaceutical composition thereof, wherein the chimeric virus is produced by a method comprising culturing a host cell which comprises:
   a Simian Immunodeficiency Virus (SIV) Gag-Pol nucleic acid sequence under control of an expression control sequence, wherein said SIV Gag-Pol nucleic acid sequence encodes an SIV capsid,
   a vector comprising a Human Immunodeficiency Virus type 2 (HIV-2) packaging signal and the heterologous nucleic acid sequence under control of an expression control sequence,
   SIV accessory genes necessary for viral assembly, and
   a viral envelope coding sequence under control of expression control sequences;
   wherein said culturing results in said vector being packaged in the SIV capsid to produce the chimeric virus.

2. The method according to claim 1 wherein the individual is a human or non-human primate.

* * * * *

SEQUENCE LISTING

```
<160> NUMBER OF SEQ ID NOS: 3

<210> SEQ ID NO 1
<211> LENGTH: 28
<212> TYPE: DNA
<213> ORGANISM: Human immunodeficiency virus type 2

<400> SEQUENCE: 1
aacaaaccac gacggagtgc tcctagaa                                        28

<210> SEQ ID NO 2
<211> LENGTH: 85
<212> TYPE: DNA
<213> ORGANISM: Simian immunodeficiency virus

<400> SEQUENCE: 2
agaactcctg agtacggcct gagtgaaggc agtaagggcg gcaggaacca accacgacgg     60
agtgctccta taaaggcgca ggtcg                                           85

<210> SEQ ID NO 3
<211> LENGTH: 50
<212> TYPE: DNA
<213> ORGANISM: Simian immunodeficiency virus

<400> SEQUENCE: 3
gaaatagctg tcttgttacc aggaagggat aataagatag attgggagat                50
```